United States Patent [19]
Angres

[11] Patent Number: 4,508,106
[45] Date of Patent: Apr. 2, 1985

[54] MICROSURGICAL METHOD FOR APPLYING PERMANENT EYELID LINER

[75] Inventor: Giora G. Angres, North Las Vegas, Nev.

[73] Assignee: Angres Clinic, Ltd., North Las Vegas, Nev.

[21] Appl. No.: 545,114

[22] Filed: Oct. 24, 1983

Related U.S. Application Data

[63] Continuation-in-part of Ser. No. 454,146, Feb. 14, 1983, abandoned.

[51] Int. Cl.³ .............................................. A61B 17/00
[52] U.S. Cl. .............................. 128/1 R; 128/303 R; 81/9.22; 132/88.7
[58] Field of Search .................. 128/316, 76.5, 303 R, 128/1 R, 355; 604/22, 46, 47, 290, 294, 310; 81/9.22; 132/88.7; 427/1, 2

[56] References Cited

U.S. PATENT DOCUMENTS

| | | | |
|---|---|---|---|
| 1,850,540 | 3/1932 | Erickson | 132/88.5 |
| 1,974,825 | 9/1934 | Lovie | 132/1 |
| 2,438,646 | 3/1948 | Pulliam | 128/20 |
| 3,485,251 | 12/1969 | Brunet | 132/53 |
| 3,789,856 | 2/1974 | Bomba | 132/88.5 |
| 3,884,232 | 5/1975 | Braun | 128/260 |
| 4,033,364 | 7/1977 | Inzana | 132/88.5 |
| 4,204,438 | 5/1980 | Binaris et al. | 81/9.22 |

Primary Examiner—Michael H. Thaler
Attorney, Agent, or Firm—Laff, Whitesel, Conte & Saret

[57] ABSTRACT

A method and apparatus for applying a permanent or semi-permanent cosmetic eye liner to the edge of an eye lid by implanting a pigment solution by surgical procedure along the edge of the eye lid and/or the lash line. The eye lid is anesthetized and stabilized, and a series of needles coated with a pigment solution is inserted into the edge of the eye lid to implant the pigment solution into the dermal and/or epidermal layer of skin beneath the eye lid edge. A guide mechanism is provided to guide the implantation of pigment solution in the proper, pre-selected location.

7 Claims, 12 Drawing Figures

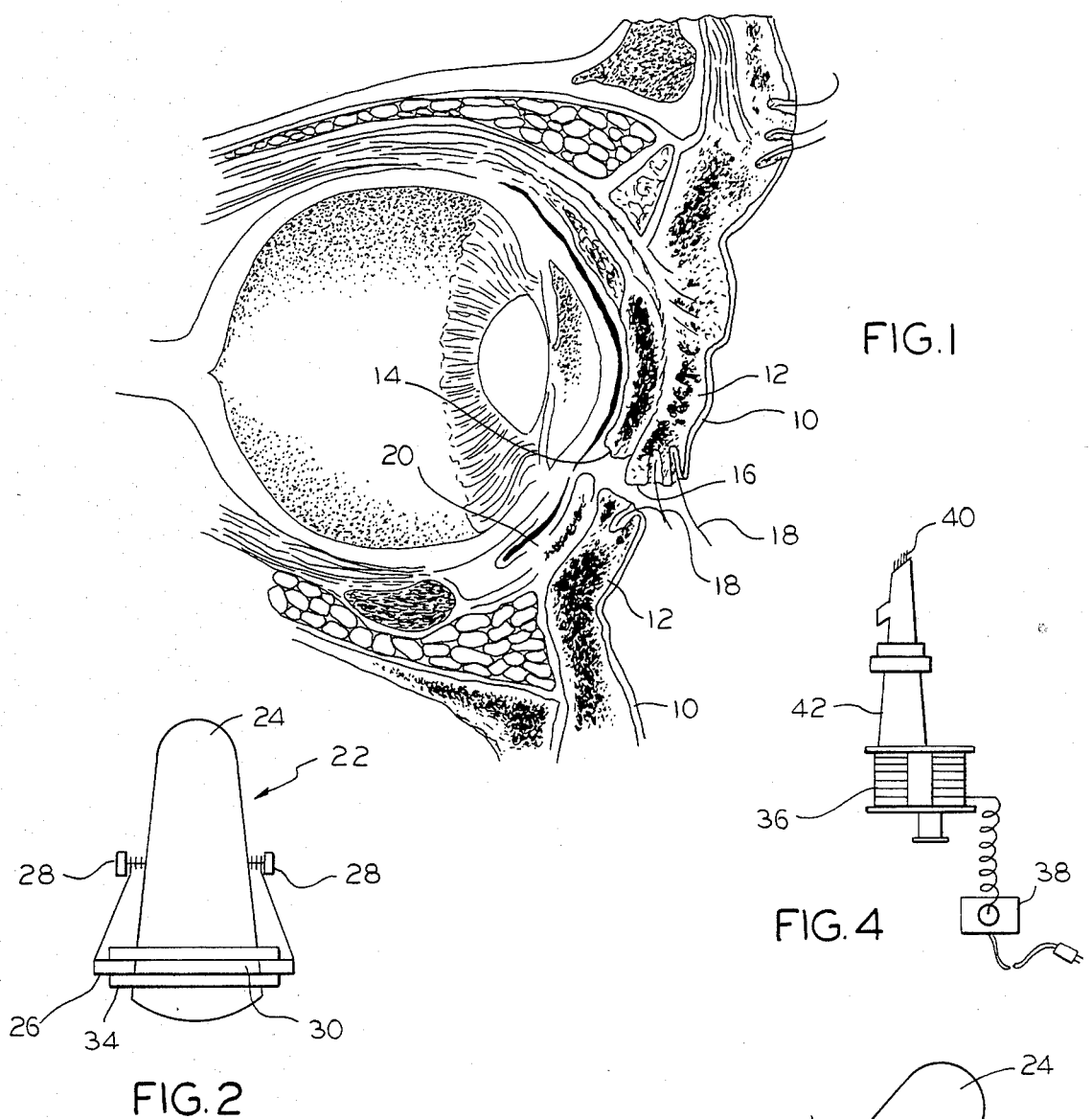
FIG. 1
FIG. 4
FIG. 2
FIG. 3
FIG. 5
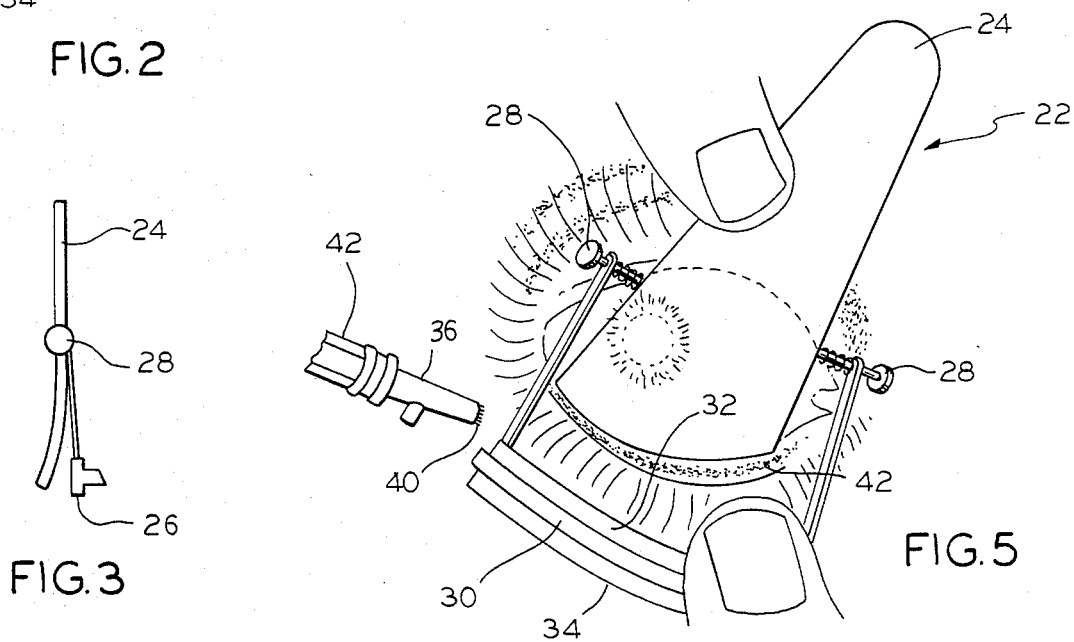

MICROSURGICAL METHOD FOR APPLYING PERMANENT EYELID LINER

This is a continuation-in-part of Ser. No. 454,146, filed Feb. 14, 1983, now abandoned.

The present invention relates generally to a method and apparatus to apply a permanent cosmetic eye lid liner, and in particular to a novel method and apparatus for safely injecting a coloring medium into the edges of the eye lid to produce a cosmetic enhancement of the eye area.

BACKGROUND OF THE INVENTION

The eye-lids are thin curtains of skin, conjunctiva, and striated and smooth muscle that contain a plate of fibrous tissue known as the tarsus. The lids function in distributing tears over the anterior surface of the eye and in limiting the amount of light entering the eye. Thus, the primary function of the lid is to protect the eyeball.

Since ancient times, the eyes have also been a significant means of attraction between the genders. Enhancement of the eye by framing the lids with exotic paint or coloring has been known to every culture since the days of Cleopatra, and pencil and liquid eye liners and mascara form an important part of today's cosmetic market. Practically every woman enhances the outline of her eye before going out socially or otherwise.

However, up to now, certain women could not wear eye liner because of several reasons. Some women have visual impairments such as cataracts or the like and cannot see well enough to apply eye liner using conventional means without taking a chance that the sharp edge of an application instrument will pierce the eye. Yet other women may have physical handicaps affecting their hands which prevent them from applying eye liner with a steady stroke. In some instances, a wearer of contact lenses cannot wear conventional eye make-up.

Thus, there are numerous women whose physical appearance and emotional well being suffer because of their lack of the ability to enhance their appearance by using normal eye liner make-up. Therefore, an object of the present invention is to provide a procedure and apparatus for cosmetic surgery to enhance the appearance of the eyes by surgically implanting color pigments under the skin layers of the lash line or lid margin of the eyes.

Another object of the present invention is to provide an apparatus for simultaneously holding the eye lid in place and acting as a guide for the implantation of colored pigments beneath the skin of the lash line or lid margin.

Still another object of the present invention is to provide a procedure for implanting color pigments beneath the skin of the lash line or lid margin, which procedure is performed under a microscope to provide greater safety and efficiency in the implantation process.

Yet another object of the present invention is to provide a procedure for permanently implanting colored pigments into the dermal and/or epidermal layer of the lash line or lid margin, which includes methods of application that prevent smearing or smudging of the eye liner, and which avoids discomfort to the patient to whom the procedure is being applied.

A further object of the present invention is to provide a permanent and/or semi-permanent eye liner to the dermal and/or epidermal layer of the skin, whereby additional colored pencil or liquid eye liner can be applied directly to the skin surface over the permanent eye liner.

Another object of the present invention is to provide an apparatus for implanting colored pigments into the dermal and/or epidermal layer of the eyelash line or lid margin, which apparatus includes a novel reciprocating needle structure in combination with an enveloping cone which surrounds and protects the needle structure, ensures the proper degree of penetration of the needle structure into the skin, and stores pigment solution adjacent the needle structure by means of capillary action.

These and other objects and features accomplished by the present invention will be better understood with reference to the following summary of the invention, drawings, and detailed description of a preferred embodiment thereof.

SUMMARY OF THE INVENTION

A method is provided for applying a permanent cosmetic liner to the edge of an eye lid comprising the steps of anesthetizing the portion of the eye lid in the area adjacent the edge of the lid, stabilizing the portion of the eye lid to which the permanent liner is to be applied, and penetrating the skin with pigment solution along a line defining the intended location of the eye liner and into the deep layers of the skin and/or lid margins and lash line.

The apparatus for penetrating the skin with pigment solution comprises a unique reciprocating needle structure in combination with an enveloping cone structure which protects the needles, ensures proper penetration, and stores pigment solution.

Also, apparatus is provided to stretch and stabilize the eye lid in preparation for a surgical procedure in which a permanent eye liner is implanted in the edge of the eye lid. The apparatus consists of an eye protector element and a guide element, whereby a device for implanting a pigment solution follows the guide element to ensure that the pigment is implanted in the proper pre-selected location of the eye lid.

BRIEF DESCRIPTION OF THE DRAWINGS

FIG. 1 illustrates in cross section a typical eye and lid construction, showing the approximate position in the dermal layer of the lids where the colored pigments are implanted by the disclosed procedure;

FIG. 2 is a plan view of an embodiment of a novel combination eye protector and guide device used in assocation with the procedure forming part of the present invention;

FIG. 3 is a side view of the combination eye protector and guide device illustrated in FIG. 2;

FIG. 4 is a detail view of the guide portion of the device shown in FIG. 2, illustrating a pigment application apparatus inserted through said guide;

FIG. 5 is a schematic illustration of the procedure of the present invention being applied to an eye lid, using the combination eye protector and guide of FIG. 2;

DESCRIPTION OF THE PREFERRED EMBODIMENT

Figure 6:
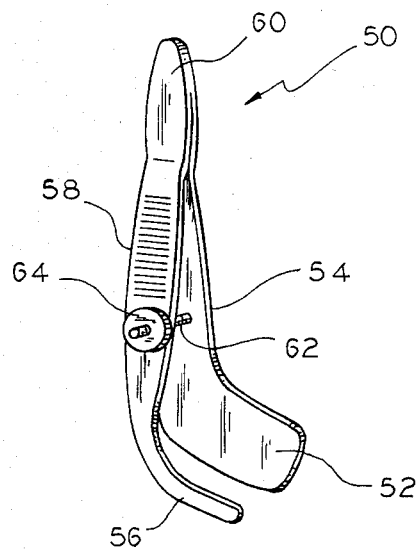
FIG. 6 is a plan view of a second embodiment of a combination guide device used in association with the present invention.

FIG. 1 is a schematic cross section of the eyelid and anterior orbit. Both the upper and lower eyelids have an epidermal layer 10 and a dermal layer 12 immediately beneath the epidermal layer 10. A tarsal portion 14 is located beneath the dermal layer 12 of both the upper and lower lid, and ends adjacent the lid margins 16. The tarsal portion 14 of each lid is involved in reflex blinking. Both upper and lower lid margins 16 contain a line of pores through which lashes 18 extend. The line of these lashes extending laterally across each lid margin 16 is known as the lash line. The lid margins 16 contain the mucocutaneous junction of skin 10 and conjunction 20 called the gray line.

The present invention relates to dermography, which is the process of drawing on the skin, and more particularly on the inner and/or outer lid margins, such as along the lash line or gray line. In describing the present invention, first the method of applying a permanent eye liner to the lash line or gray line will be described.

The patient is first prepared and draped for normal outpatient surgical procedures. Next, an akinesia or local anesthetic is applied to immobilize the lid and to relax the tarsal muscle 14 thereby preventing blinking during the surgical procedure. Any intradermal anesthetic can be used, such as solutions of novocaine, xylocaine, or the like. In the preferred embodiment, an anesthetic solution is used comprising 2 cc 2% xylocaine, epinephyrine, and hyalurondaze. The epinephrine functions to constrict the blood vessels to decrease the possibility of bleeding. The hyalurondaze functions as a spreading factor to aid in spreading the local anesthetic faster and more evenly through the lid tissue by opening the dermal tissue under the skin. This permits a smaller needle to be used for implantation; and allows for a lesser degree of skin penetration.

The anesthetic solution is injected by a needle in or around the eye lid area. In the preferred embodiment, a 27 gauge needle was used to make an interdermal wheal 1 mm on the outside of the lateral or outside angle of the upper and lower lid. After the needle has been removed, the skin is massaged for a few minutes to allow skin edema or thickening to settle.

Next, a sterile tipped marking pen is used to mark and delineate the site on the lid margins where the implantation is to be applied, according to the patient's specifications. The eye lid is held in position such that the margin to be implanted is exposed to the application process. A lubricant such as decadron 1% ophthalmic ointment is applied topically to the site to be implanted. The lid is adequately stretched and stabilized, either by hand or by using a device such as one of the two combination eye protector and guide devices illustrated in FIGS. 2–7.

A series of applicator needles are next coated with a pigment solution to be inserted beneath the skin of the margin of the eyelid. In the preferred embodiment, a tattoo-like applicator may be used, calibrated to penetrate only a short distance into the skin, such as 1/54th of an inch. This ensures that the pigment solution is inserted into the dermal, and not the epidermal, layer of tissue. An even 1.5 mm line is next drawn with a nasal to temporal motion across the eye lid, or temporal to nasal, or a combination of both.

The same procedure is then applied to the fellow lid of the same eye, and then the same procedures are applied to the upper and lower lids of the other eye. An antiseptic ointment is then placed on the lids to aid in the prevention of swelling and secondary infection.

In the preferred embodiment, the above procedures were accomplished under a microscope. However, as the operator gains additional skill through experience in performing the above-described process, the use of a microscope may not be necessary.

Part of the procedure stated above requires stretching and stabilizing the eyelid during injection of the pigment solution. FIGS. 2–5 illustrate a first embodiment of a combination eye protector and guide device which is adapted to stretch and stabilize the skin, as well as protect the eye and assist in guiding the implantation needle. The device is generally designated by the numeral 22, and comprises an eye protective element 24 pivotally connected to a lid guide element 26 by means of adjustable screws 28. The guide 28 has a slit portion 30 extending from one side to the other, with shield or screen elements 32, 34 extending above and below the lengthwise extent of slit portion 30. The relative position of guide 26 relative to eye protective element 24 can be stabilized by tightening screws 28.

FIG. 4 illustrates an implanting device 36 controlled by a rehostat 38, and having a series of implantation needles 40 extending from a body portion 42. Needles 40 are adapted to extend through slit 30 of guide 26, and contact the eye lid for implantation of the pigment as described above.

FIG. 5 is a schematic illustration of the device 22 placed adjacent an eye lid which is about to be implanted with pigmentation by means of implanting device 36. The lower edge of eye protective element 24 is placed inside the gray line 42 of an eye lid to stretch the lid and at the same time provide a protective screen over the eye. Shield elements 32, 34 are pressed against the eye lid, which extends the lid and exposes the proper area to be implanted. Screws 28 are tightened so that guide 26 and protective element 24 form a single, rigid entity. Next, needles 40 are extended into slit 30 of guide 26, and the needles are moved laterally along the length of slit 30 until the appropriate length of eye lid is impregnated. Guide 26 is set such that the implanted pigmentation extends along the eye lid margin or along the lash line. After completion of the implantation process, screws 28 are loosened, and the device 22 is removed from the eye.

Figure 7:
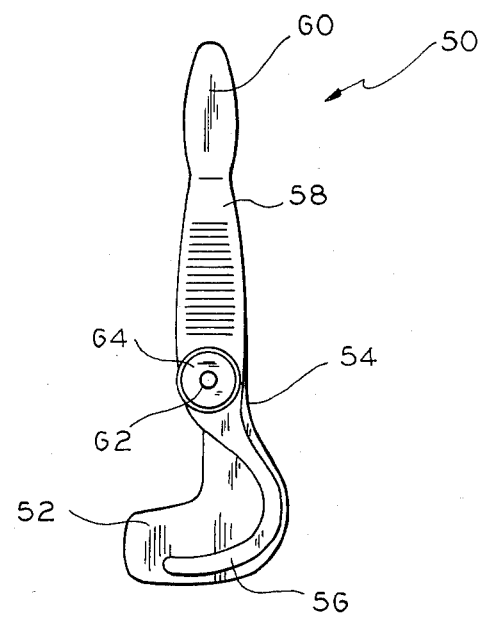
FIG. 7 is a side view of the device illustrated in FIG. 6.

FIGS. 6 and 7 disclose a second embodiment of a guide device that can be used in association with the above-described process. The device is generally designated by the numeral 50 and has a tweezer-like configuration having a flat skin pressing element 52 forming the end of a first arm 54, and a curved guide bar 56 forming the end of a second arm 58. The opposite ends of each arm 54, 58 are joined together in a spring-like connection 60. A threaded shaft 62 extends from arm 54 to an aperture in arm 58, and a thumb wheel 64 engages threaded shaft 62 to form a means for adjusting and fixing the distance between pressing element 52 and guide bar 56.

When used, device 50 is held adjacent the eye lid such that element 52 presses against the eye lid and stretches the lid to expose the area to be implanted. Thumb wheel 64 is then rotated to properly locate guide bar 56 relative to element 52. Next, implanting device 36 is moved into position adjacent the area to be implanted, using guide bar 56 as a means to stabilize and control the lateral movement of implanting device 36 and needles 40. The procedure set forth above is then continued.

Figure 8:
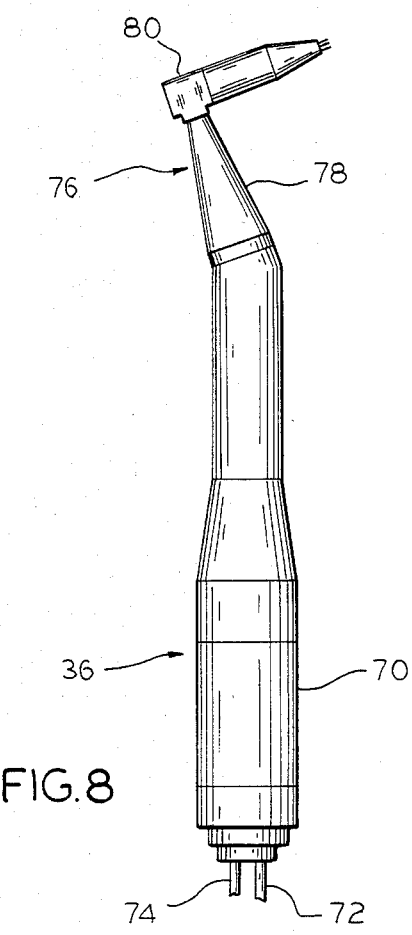
FIG. 8 is a plan view of the reciprocating drive mechanism, needle and cone structure for implanting pigment into the skin in accordance with the teachings of the present invention.

FIGS. 8-12 disclose a preferred embodiment of the implanting device 36 illustrated in FIG. 4. Referring first to FIG. 8, device 36 includes a hollow handle 70 which is adapted to be manually gripped. In this embodiment, the device 36 is pneumatically controlled, and air inlet and outlet passages 72, 74 are provided to operate an air-driven motor (not shown) in handle 70. Other types of power drive means may be utilized if desired. Opposite air passages 72, 74, handle 70 includes an operating head portion 76 which is angled from the center line of handle 70 for ease of handling. However, the angled configuration of head portion 76 is a matter of choice, and can be modified as the user sees fit.

Figure 9:
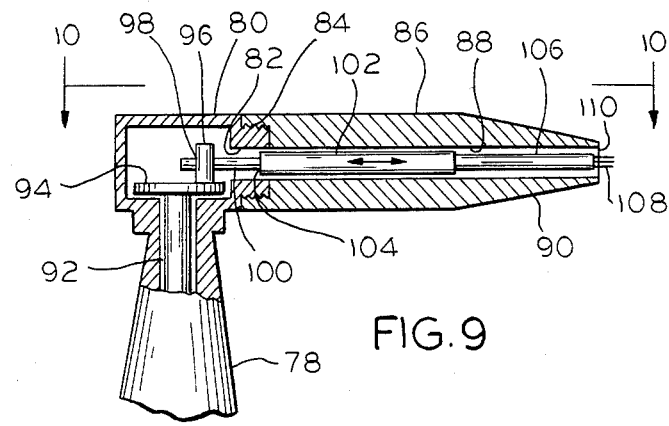
FIG. 9 is a schematic detail view of the reciprocating drive mechanism for the needle structure, the needle structure per se, and the protective cone which envelopes the needle structure.

Head portion 76 includes a hollow stem 78 to which is attached a hollow housing element 80. As best seen in FIG. 9, housing element 80 includes an aperture 82 leading from one side thereof, and a threaded circular flange 84 around aperture 82. A hollow cone element 86 having threads at one end corresponding to the threads on flange 84, is removably attached to flange 84 and housing element 80. Cone element 86 includes hollow portion 88 extending along its length, and a tapered outer end 90.

Inside hollow stem 78 is a rotating shaft 92 which is driven by the air driven motor (not shown) inside handle 70. The end of shaft 92 extends into housing element 80 and is attached to circular plate 94. A connecting pin 96 is located off-center on plate 94, and includes an aperture 98 therethrough. Extending through aperture 98 at one end and through aperture 82 at the other end is a connecting rod 100 which is fixed in aperture 98 and is flexibly attached to a needle structure connecting piece 102 at pivot point 104, for purposes to be described.

The opposite end of mounting piece 102 includes a needle mount member 106 which is removably but firmly attached to connecting piece 102. A series of needles 108 project from the end of needle mount member 106, and extends slightly beyond the opening 110 at the end of cone element 86 when plate 94 and connecting pin 96 are in the position shown in FIGS. 9 and 10.

Figure 12:
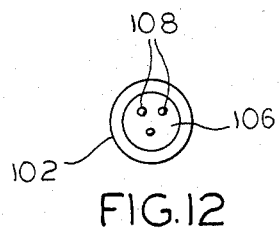
FIG. 12 is an end view of the needle structure of the present invention, taken along the line 12—12 in FIG. 11.
Figure 11:
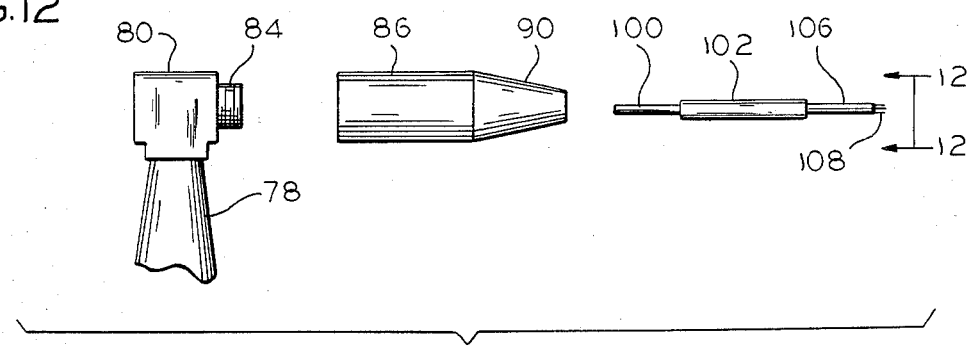
FIG. 11 is an exploded view of the reciprocating drive head, cone, and needle structure illustrated in FIG. 9.

In the preferred embodiment, needles 108 comprise three needle elements firmly held to the circular end of mount member 106, as best seen in FIG. 12. The use of three needles in the array shown in FIG. 12 has proven to provide excellent results, however, other needle arrays may be utilized without departing from the spirit of the invention.

Figure 10:
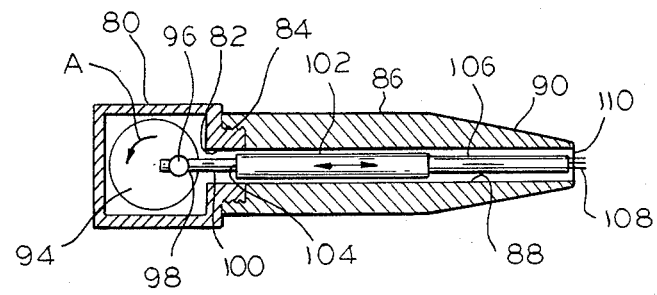
FIG. 10 is a schematic top detail view of the structure shown in FIG. 9, taken along the line 10—10.

The operation of the device illustrated in FIGS. 8-12 is commenced by actuating air through inlet 72 to drive the air motor in handle 70 and rotate shaft 92 and circular plate 94 in the direction shown by arrow A in FIG. 10. As pin 96 rotates with plate 94, connecting rod 100 moves back and forth through aperture 82 thereby imparting relatively rapid reciprocal motion to needle mount member 106 and needles 108. Connecting rod 100 is also subject to slight side-to-side motion as the rotating motion of shaft 92 is converted to reciprocal motion by pin 96, and pivot connection 104 accommodates this side-to-side motion.

When using the device illustrated in FIGS. 8-12, the operator, who is preferably a trained and licensed physician, dips the end 90 of cone 86 in an aqueous pigment solution. Preferably, cone 86 is dipped into the solution far enough to allow the aqueous solution to enter hollow portion 88 of the cone where the fluid is retained by capillary action. Obviously, needles 108 are also immersed in the aqueous solution, which is held in the space between the needles 108 also by capillary action. Thus, the liquid pigment storage capacity of the subject implement is increased by virtue of this double capillary effect.

After dipping the cone into the aqueous pigment solution, the end of cone 86 comprising needles 108 is held adjacent the eyelid, which has been properly stretched and stabilized according to the method and apparatus described above in conjunction with FIGS. 2-5. Air is supplied to the reciprocating motor drive in handle 70, and needles 108 are reciprocally driven rapidly and with a relatively short stroke. The distance between the tip of end 90 of cone element 86 and the outer end of needles 108 is calibrated to penetrate the skin a preselected desired amount, such as 1/54th of an inch, as stated above. The handle 70 is then drawn across the eyelids as mentioned previously.

The foregoing detailed description has been given for clearness of understanding only and no unnecessary limitations are to be understood therefrom. Modifications of the present invention may be made by those skilled in the art without departing from the spirit of the invention.

I claim:

1. A method of applying a permanent cosmetic liner to the edge of an eye lid comprising the steps of anesthetizing the portion of the eye lid in the area adjacent the edge of said eye lid; stabilizing the portion of the eye lid to which said liner is to be applied; penetrating the skin with pigment solution along a line on the eye lid defining the intended location of said liner.

2. The method of claim 1 wherein the step of penetrating the skin with pigment solution is performed under a microscope.

3. The method of claim 1 wherein said step of anesthetizing said eye lid immobilizes said eye lid, relaxes the tarsal muscle of the eye to prevent blinking during application of said pigment solution, and anesthetizes the eye lid area.

4. The method of claim 1 wherein said step of anesthetizing said eye lid consists of injecting a solution of 2 cc 2% xylocaine, epinephrine and hyalurondaze around the eye lid area.

5. The method of claim 1 including the additional step of marking the site on the portion of the eye lid where the penetration of the skin is to take place subsequent to the step of stabilizing said portion of the eye lid.

6. The method of claim 1 including the step of lubricating the portion of the eye lid to be penetrated prior to the step of penetrating said portion of said eye lid.

7. The method of claim 1 wherein the step of penetrating the skin with pigment solution comprises coating a series of applicator needles with said pigment solution and inserting said coated needle into said portion of said eye lid to an extent whereby said pigment solution is applied to the dermal or epidermal layer of said eye lid.

* * * * *